United States Patent
Muneshima

(10) Patent No.: US 9,211,097 B2
(45) Date of Patent: Dec. 15, 2015

(54) PHYSIOLOGICAL MONITORING APPARATUS

(71) Applicant: NIHON KOHDEN CORPORATION, Tokyo (JP)

(72) Inventor: Rie Muneshima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/163,995

(22) Filed: Jan. 24, 2014

(65) Prior Publication Data

US 2014/0218198 A1    Aug. 7, 2014

(30) Foreign Application Priority Data

Feb. 4, 2013   (JP) .................................. 2013-019766

(51) Int. Cl.
   *G08B 23/00* (2006.01)
   *A61B 5/00* (2006.01)
   *A61B 5/0205* (2006.01)
   *G08B 21/04* (2006.01)

(52) U.S. Cl.
   CPC ............... *A61B 5/746* (2013.01); *A61B 5/0205* (2013.01); *A61B 5/741* (2013.01); *G08B 21/0453* (2013.01)

(58) Field of Classification Search
   CPC .... A61B 5/0022; A61B 5/7271; A61B 5/002; A61B 5/746
   USPC ...................... 340/573.1, 539.12, 506, 13.24; 600/300; 128/904
   See application file for complete search history.

(56) References Cited

U.S. PATENT DOCUMENTS

| 4,590,934 A | 5/1986 | Malis et al. |
| 4,981,139 A * | 1/1991 | Pfohl ............................ 600/484 |
| 2005/0080403 A1 | 4/2005 | Takahashi |
| 2005/0128184 A1 * | 6/2005 | McGreevy ..................... 345/156 |
| 2007/0156031 A1 * | 7/2007 | Sullivan et al. ................ 600/300 |
| 2010/0177100 A1 * | 7/2010 | Carnes et al. ................. 345/440 |
| 2011/0011708 A1 * | 1/2011 | Ellafrits ....................... 200/86.5 |
| 2013/0181833 A1 | 7/2013 | Al-Ali |

FOREIGN PATENT DOCUMENTS

JP    2007-215581 A    8/2007

OTHER PUBLICATIONS

The extended European Search Report for the related European Patent Application No. 14152642.6 dated Mar. 27, 2014.

* cited by examiner

*Primary Examiner* — Phung Nguyen
(74) *Attorney, Agent, or Firm* — Kenealy Vaidya LLP

(57) ABSTRACT

A physiological monitor has notification unit for notifying an alarm; an alarm determination section that determines whether or not to generate an alarm by comparing measured physiological parameter pertinent to a patient with a predetermined threshold value, an alarm control section that lets the notification unit notify an alarm when the alarm determination section has determined to generate an alarm, and a foot switch that, when being trodden, outputs to the alarm control section an alarm inactivate signal for inactivating the alarm, wherein the alarm control section inactivates the alarm being generated from the notification unit in accordance with the alarm inactivate signal output from the foot switch and lets the notification unit notify by voice details of physiological parameter for which the alarm is being generated.

3 Claims, 5 Drawing Sheets

PHYSIOLOGICAL MONITORING APPARATUS

BACKGROUND

The presently disclosed subject matter relates to a physiological monitoring apparatus capable of notifying occurrence of abnormalities or changes in a patient's condition.

An apparatus which has been hitherto used widely measures physiological parameters indicating vital signs of a patient, determines if the measured physiological parameters are abnormal or have any changes, and generates a notice by means of an alarm when having determined that the measured physiological parameters are abnormal or have any changes.

For instance, Patent Document JP-A-2007-215581 provided below discloses a physiological monitoring apparatus that determines if physiological parameter input by input means are a normal value or an abnormal value and that generates an alarm by making an alarm indicator light up when having determined the physiological parameter as an anomalous value.

However, in relation to the physiological monitoring apparatus disclosed in connection with Patent Document JP-A-2007-215581, when an alarm is generated as a result of a change in a patient's condition, a healthcare personnel hitherto has to watch a display screen of a monitor in order to ascertain details of the alarm by suspending medical treatment which the healthcare personnel is performing at that point. In addition, in order to inactivate a warning (alarm) generated by the alarm indicator, the healthcare personnel must touch the alarm indicator by hand. For this reason, when performing medical care that cannot be interrupted halfway (for instance, surgical operation), the healthcare personnel has hitherto encountered difficulty in inactivating the alarm.

SUMMARY

This presently disclosed subject matter provides a physiological monitoring apparatus that enables a healthcare personnel to easily inactivate an alarm even in the middle of performing medical care with the healthcare personnel's hands full, and that allows the healthcare personnel to ascertain details of the alarm without fail.

It is therefore an aspect of the presently disclosed subject matter to provide a physiological monitoring apparatus comprising: notification unit configured to notify an alarm; an alarm determination section configured to determine whether or not to generate the alarm by comparing measured physiological parameter pertinent to a patient with a predetermined threshold value; an alarm control section configured to let the notification unit generate the alarm when the alarm determination section has determined to generate the alarm; and a foot switch configured to, when being trodden, output to the alarm control section an alarm inactivate signal for inactivating the alarm, wherein the alarm control section inactivates the alarm being notified by the notification unit in accordance with the alarm inactivate signal output from the foot switch, and lets the notification unit notify by voice a content of physiological parameter from which generating the alarm has been determined.

In the physiological monitor, when the foot switch is trodden in a case where a plurality of sets of physiological parameter by which the alarm is being generated are existing, the alarm control section may let the notification unit notify by voice contents of a plurality of sets of physiological parameter from which generating the alarm has been determined.

In the physiological monitor, when letting the notification unit sequentially notify contents of the plurality of sets of physiological parameter, the alarm control section may let the notification unit notify the physiological parameter in a descending order from physiological parameter that indicates high urgency for medical treatment.

DETAILED DESCRIPTION OF EMBODIMENTS

An embodiment of a physiological monitoring apparatus of the present subject matter is hereunder described by reference to the accompanying drawings.

Figure 1:
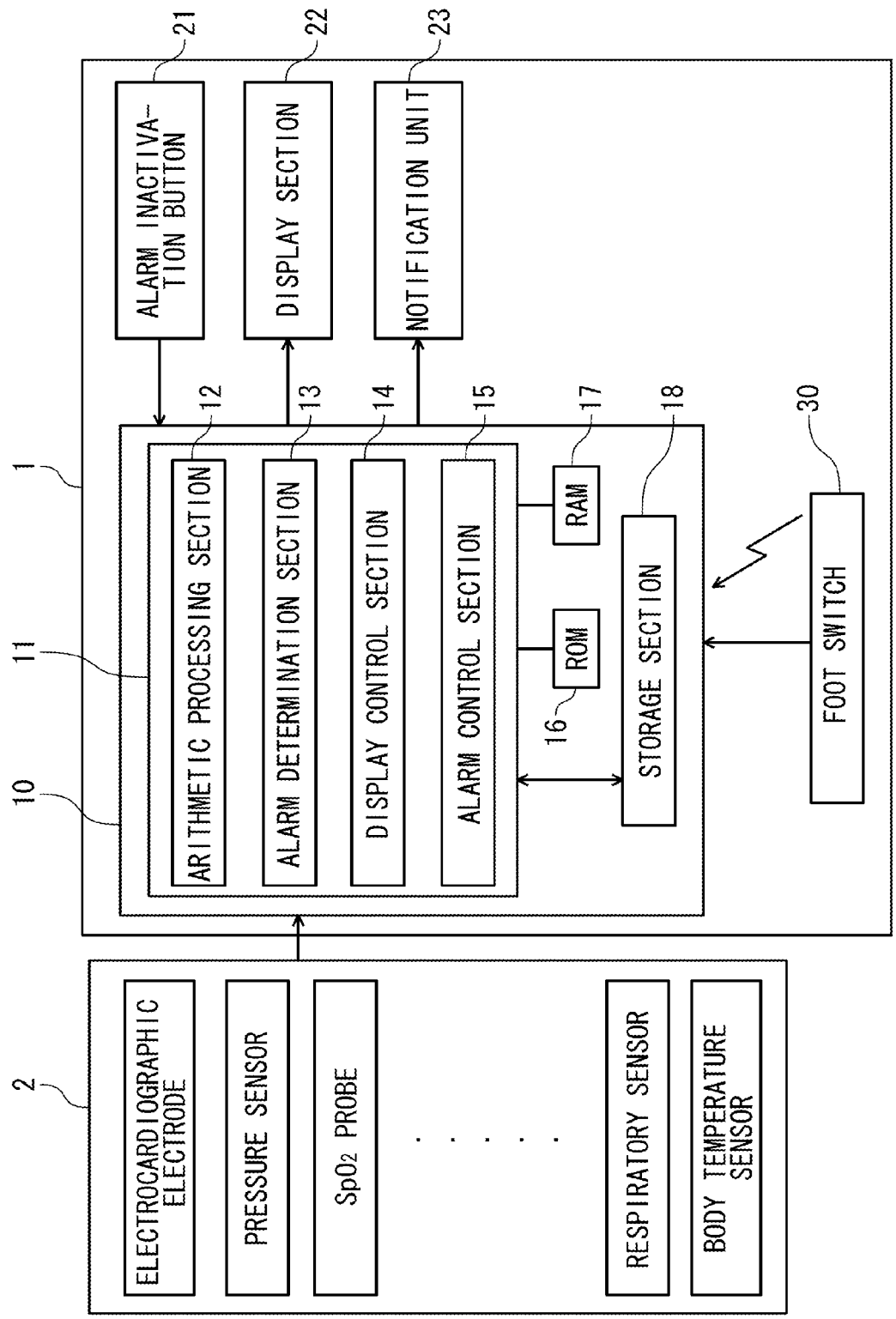
FIG. 1 is a block diagram illustrating a configuration of a physiological monitoring apparatus according to one aspect of the subject matter.

FIG. 1 is a block diagram illustrating a configuration of a physiological monitoring apparatus 1. The physiological monitoring apparatus 1 is an apparatus that computes physiological parameter acquired from a test subject (a patient) and that displays or notifies a computation result. The physiological monitoring apparatus 1 may be used as a so-called bedside monitor to be installed for each patient. In particular, the physiological monitoring apparatus 1 may be used in a situation in which a healthcare personnel's hands are full because the healthcare personnel is in the course of performing medical care with the use of hands and fingers; for instance, in which the healthcare personnel is performing surgery of the patient or in which the healthcare personnel is performing medical treatment in a neonatal intensive care unit (NICU).

The physiological monitoring apparatus 1 is connected to physiological parameter acquisition unit 2 intended for acquiring physiological parameter, such as an electrocardiogram, a heart rate (a pulse rate), an invasive blood pressure value, respiration, and a body temperature. As illustrated in; for instance, FIG. 1, sensors, like electrocardiographic electrodes and a pressure sensor for measuring an invasive blood pressure value, an SpO2 probe, a respiratory sensor, a body temperature sensor, may exemplify the specific physiological parameter acquisition unit 2. The physiological parameter acquisition unit 2 is attached to the test subject, and physiological parameter acquired by the physiological parameter acquisition unit 2 are input to the physiological monitoring apparatus 1.

The physiological monitoring apparatus 1 comprises a control section 10 that controls operation of the monitor, an alarm inactivate button 21 that inactivates (stops) a generated alarm (warning), a display section 22 that displays measured physiological parameter, alarm condition, and the like, notification unit 23 that notifies an alarm and physiological parameter, and a foot switch 30. Physiological parameter acquired by the physiological parameter acquisition unit 2 are input to the control section 10 of the physiological monitoring apparatus 1.

The control section 10 includes the physiological parameter acquisition unit 2, the alarm inactivate button 21, and a CPU (Central Processing Unit) 11, as a principal constituent section, that controls operation of individual sections of the physiological monitor 1 in accordance with information and a signal that are input from the foot switch 30. In addition, the control section 10 includes a storage section 18 that stores physiological parameter which are generated by having a signal acquired by the physiological parameter acquisition unit 2 processed by an unillustrated filter or an A/D conversion circuit, and the like.

The CPU 11 performs various numerical computations, information processing, and others, in accordance with a program stored in ROM 16, thereby controlling operation of the physiological monitoring apparatus 1. The CPU 11 uses RAM 17 as an area for storing various sets of data.

The CPU 11 includes an arithmetic processing section 12, an alarm determination section 13, a display control section 14, and an alarm control section 15. The CPU 11 functions as the respective sections 12, 13, 14, and 15, performs numerical calculation and information processing of the measured physiological parameter, and controls operation of the individual sections in accordance with computation and processing results.

The arithmetic processing section 12 is a processing section that analyzes and computes a signal of the physiological parameter acquired by the physiological parameter acquisition unit 2. Specifically, the arithmetic processing section 12 arithmetically processes electric signals of respective pieces of the acquired physiological parameter, generating physiological signals to be monitored (a heart rate signal HR, an invasive blood pressure value ART, an oxygen saturation SpO2, and the like, that are derived from an electrocardiographic signal). These physiological signals generated by the arithmetic processing section 12 are stored in the storage section 18.

The alarm determination section 13 determines a status of each of the physiological signals generated by the arithmetic processing section 12, determining whether to generate an alarm. Specifically, the alarm determination section 13 determines whether or not measured physiological parameter pertinent to a patient indicates abnormal condition. Issuance of an alarm is determined by comparing a value of a generated physiological signal with a preset threshold value for the physiological signal. The threshold value is a value that represents, for example, a critical threshold, a serious threshold, and so on, for the patient and that is set by the healthcare personnel in accordance with a medical condition of the patient to be monitored.

When the comparison result indicates that the value of the generated physiological signal exceeds the threshold value (exceeds or falls below the threshold value), the alarm determination section 13 determines that the physiological signal indicates abnormal condition, outputting a signal aimed at issuing an alarm. The alarm is a warning that notifies occurrence of an abnormality in each of parameters of the physiological parameter. The alarm is displayed on a display section 22 as will be described later, and an acoustic warning caused by a speaker sound or a visible warning caused by light of a indicator is generated by way of the notification unit 23.

The display control section 14 performs control operation for letting the display section 22 display physiological parameter measured by the physiological parameter acquisition unit 2 or a physiological signal generated by the arithmetic processing section 12, and a determination result made by the alarm determination section 13. In addition to loading data to be displayed from the storage section 18 and causing the display section 22 to display the thus-read data, the display control section 14 causes the display section 22 to display the data in real time. The display control section 14 transmits the data to be displayed to the display section 22 along with a control signal for controlling a display content.

In accordance with the signal output from the alarm determination section 13 (the signal aimed at issuing an alarm), the alarm control section 15 controls the notification unit 23. When the alarm determination section 13 has determined that the physiological signal indicates abnormal condition and output the signal aimed at issuing an alarm, the alarm control section 15 outputs an alarm by way of the notification unit 23, thereby generating a notification. The alarm control section 15 outputs to the notification unit 23 a control signal for activating the notification unit 23.

In accordance with an alarm inactivate signal that is output from the foot switch 30 when the foot switch 30 is trodden, the alarm control section 15 inactivates (stops) the alarm being output from the notification unit 23. When the foot switch 30 is trodden, the alarm control section 15 outputs by voice the physiological parameter by which the alarm is determined to be generated; that is, contents (e.g., a parameter of the physiological signal, a measured value, and the like) of the physiological parameter that have been determined to be abnormal, by way of the notification unit 23.

In a case where there are a plurality of sets of physiological parameter from which generating an alarm has been determined; namely, where values of the measured physiological signal in connection with the plurality of sets of physiological parameter exceed respective threshold values, the alarm control section 15 outputs by voice an alarm for each of details of the plurality of sets of physiological parameter when the foot switch 30 is trodden. The alarm control section 15 at this time outputs by voice physiological parameter, in a descending order from physiological parameter that exhibits higher urgency for medical treatment, among the plurality of pieces of physiological parameter that have exceeded respective threshold values; namely, physiological parameter that exhibit the most serious symptom of the patient.

In addition, the alarm control section 15 inactivates the alarm being output from the notification unit 23, in accordance with an alarm inactivate signal which is output from the alarm inactivate button 21 when the alarm inactivate button 21 is trodden.

The storage section 18 stores raw physiological data acquired by the physiological parameter acquisition unit 2 or parameter pertinent to a physiological signal generated by the arithmetic processing section 12, data indicating a result of comparison determination processing performed by the alarm determination section 13, and the like. Further, the storage section 18 stores a threshold value for the physiological signal which serves as a comparison criterion of an alarm issuance condition employed by the alarm determination section 13. In this regard, data indicating a result of comparative determination processing performed by the alarm determination section 13 include a value of a physiological signal that exceeds a threshold value and timing (a date and time) when the physiological signal is measured.

The alarm inactivate button 21 is a button for deactivating an alarm being output from the notification unit 23. The alarm inactivate button 21 is made up of; for instance, a push button and a touch button displayed on a display screen. The alarm inactivate button 21 is connected to the control section 10 and, when pushed (touched), outputs an alarm inactivate signal for deactivating an alarm to the CPU 11 of the control section 10.

In accordance with a control signal transmitted from the display control section 4, the display section 22 displays on the display screen the raw physiological parameter measured by the physiological parameter acquisition unit 2 or a physiological signal generated by the arithmetic processing section 12, a result of determination processing performed by the alarm determination section 13, and others. The display section 22 is connected to the control section 10 and made up of; for instance, an LCD and an organic EL. A display screen which is displayed when an alarm is generated will be described later by reference to FIG. 2 and FIG. 3.

The notification unit 23 is configured to generate an alarm when an anomaly has occurred in measured physiological parameter pertinent to the patient. The notification unit 23 is configured to output by voice contents of physiological parameter that indicate anomalous. The notification unit 23 is connected to the control section 10 and operates in accordance with a control signal transmitted from the control section 10 (the alarm control section 15). The notification unit 23 can be made up of; for instance, a speaker which outputs sounds or a indicator which outputs light.

The foot switch 30 is one for inactivating the alarm being output from the notification unit 23. The foot switch 30 is a switch for notifying contents of physiological parameter by which generating the alarm is being determined (physiological parameter that indicates anomalous status). The foot switch 30 is placed on a floor or at a position dose to the floor level so that it can be actuated by a leg. The foot switch 30 is connected to the control section 10 and configured to, when trodden with foot, output an active (ON) signal; namely, an alarm inactivate signal for inactivating the alarm being generated and notifying by voice contents of physiological parameter by which the alarm is determined to be generated. In this regard, the connection between the foot switch 30 and the control section 10 may also be wired or wireless.

An example image that will be displayed on the display screen of the display section 22 is now described by reference to FIG. 2 and FIG. 3. A heart rate (HR) 41, an invasive blood pressure value (ART) 42, an oxygen saturation (SpO2), a body temperature (TEMP) 44 are displayed as parameters of measured physiological signals on both display screens. In connection with each of parameter displays, a measured value is displayed in a large figure on the left side of the display screen, whilst a threshold value for it is displayed, while being parenthesized, in a small figure. A waveform being measured is displayed on the right side of the display screen. In relation to the display of a measured value of the ART 42, a figure on the left side of a symbol "/" designates a systolic blood pressure (SYS), whereas a figure on the right side of the symbol "/" designates a diastolic blood pressure (DIA). A parenthesized figure denotes a mean blood pressure.

Figure 2:
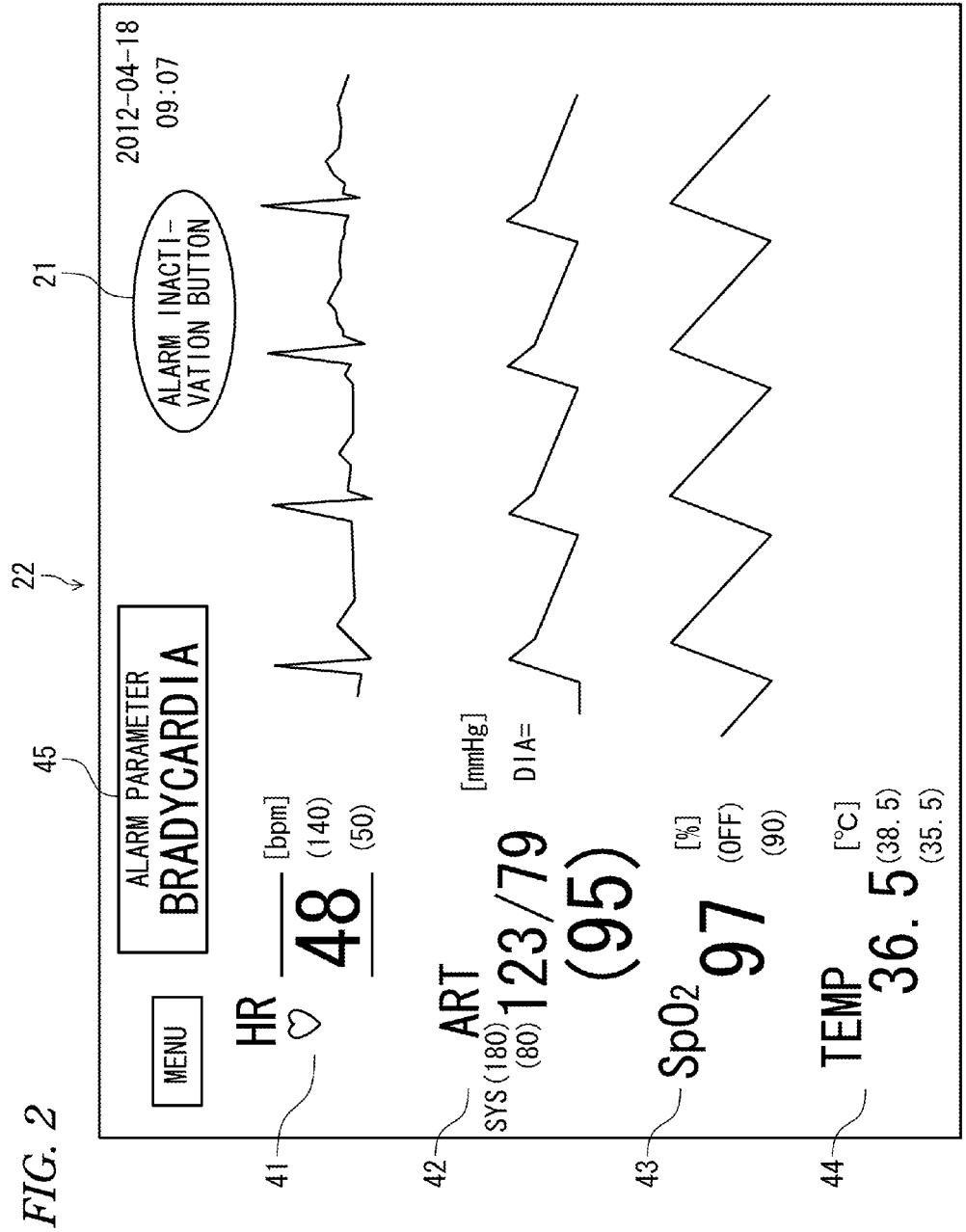
FIG. 2 is a drawing illustrating an example display screen displayed on the physiological monitoring apparatus when an alarm is generated.

FIG. 2 illustrates a case where an abnormal condition in measured physiological parameter is detected; namely, an example image to be displayed when a measured HR exceeds a preset HR threshold value. In relation to an HR threshold value of the patient, an upper limit is set to 140, and a lower limit is set to 50 as parenthesized. On the contrary, a measured HR is 48 [bpm] which falls below a lower-limit threshold value of 50 and hence becomes a subject of generating an alarm.

A message notifying occurrence of an abnormality is displayed as "BRADYCARDIA (bradycardia)" in an alarm parameter display area 45 of the display section 22. A display of the measured value "48" of the HR 41 is highlighted (with an overbar and an underbar). By visually observing the displays, the healthcare personnel can ascertain details of occurrence of the abnormality. The alarm inactivate button 21 to be touched is displayed on the display section 22, and an alarm (e.g., a warning sound output from a speaker) can be inactivated by touching the button 21.

Figure 3:
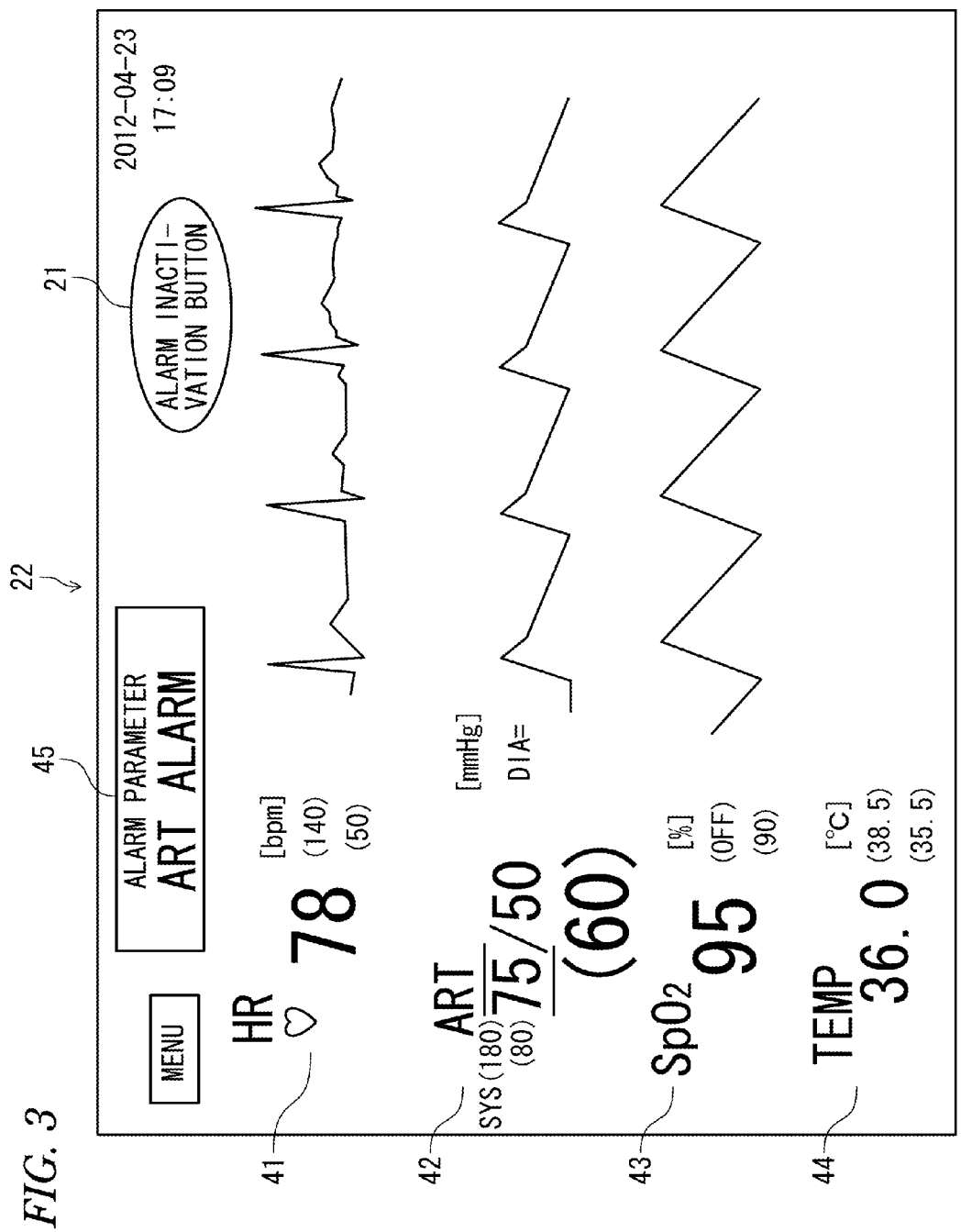
FIG. 3 is a drawing illustrating another example display screen displayed on the physiological monitoring apparatus when the alarm is generated.

FIG. 3 illustrates an example image which is displayed when an abnormality in the ART of measured physiological parameter is detected; namely, when a measured blood pressure value has exceeded a preset blood pressure threshold value. In relation to a threshold value for the ART of the patient, an upper limit of systolic blood pressure (SYS) is set to 180, whilst a lower limit of the systolic blood pressure is set to 80 as parenthesized. On the contrary, the systolic blood pressure of the measured ART is 75 [mmHg] which falls below a lower-limit threshold value of 80 and hence leads to generation of an alarm.

A message that notifies occurrence of the abnormality is displayed as "ART alarm" in the alarm parameter display area 45. A measured value "75" of the ART 42 is highlighted (with an overbar and an underbar). By visually observing the displays, the healthcare personnel can ascertain contents of occurrence of the abnormality. The alarm inactivate button 21 is displayed on the display section 22, and an alarm (e.g., a warning sound output from a speaker) can be inactivated by touching the button 21.

An example flow of operation performed when the foot switch 30 is trodden on the occurence of an alarm is now described by reference to FIG. 4 and FIG. 5.

Figure 4:
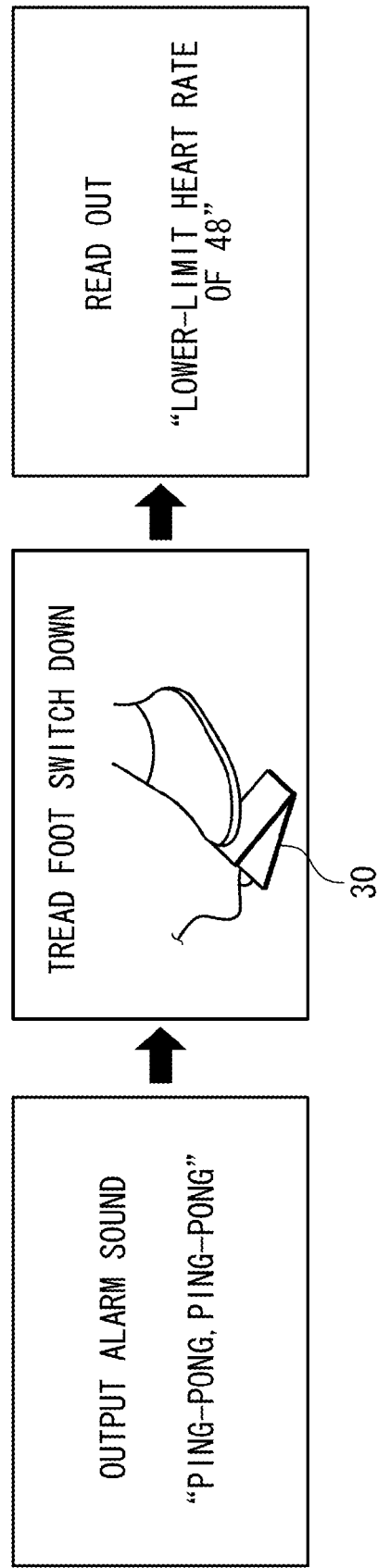
FIG. 4 is an example conceptual drawing of a flow employed when a foot switch is trodden when the alarm is generated.

FIG. 4 illustrates a flow employed when an abnormal condition has occurred in one parameter of the measured physiological parameter; namely, the heart rate (HR), in the example. The notification unit 23 outputs an alarm sound "ping-pong, ping-pong" that notifies occurrence of an abnormality. A melody of the alarm sound is set and categorized in a plurality of phases depending on urgency. For instance, the alarm sound may be set in tones of three phases; for instance, a melody "pyro-pyro, pyro-pyro" set for highest urgency; a melody "ping-pong, ping-pong" set for middle urgency; and a melody "pong-pong, pong-pong" set for low urgency.

Subsequently, the healthcare personnel treads the foot switch 30 down with foot to inactivate the alarm sound. An alarm inactivate signal is output from the foot switch 30 as a result of the foot switch 30 being trodden. The thus-output alarm inactivate signal is input to the CPU 11 of the control section 10. In accordance with the thus-input alarm inactivate signal, the alarm control section 15 inactivates the alarm sound "ping-pong, ping-pong" being output from the notification unit 23; namely, inactivates the alarm. After inactivating the alarm, the alarm control section 15 outputs by voice contents of the physiological parameter to the notification unit 23. Specifically, the contents of the physiological parameter "Lower-limit heart rate: 48" are read out by way of the speaker. The thus-read details notify that an abnormal condition in the value of the measured heart rate has been detected; that the value has fallen below the lower limit of the threshold value; and that the value is 48 [bpm].

As above, the alarm can be inactivated by means of treading only the foot switch 30 down on the occasion when the alarm sound is generated. In addition, the healthcare personnel can ascertain details of the alarm; namely, physiological parameter whose abnormal condition is detected and measured values of the physiological parameter, with the constant eye on the patient. The healthcare personnel may selectively set a preferable term as a word to be used in reading out the details. For instance, a term used for designating the heart rate (HR) varies from one healthcare center to another. Therefore, the healthcare personnel may also be given an option of selecting a preferable term from among terms including a "heart rate," a "rate," and a "cardiac beat." In addition, the number of times reading is performed can also be set to a plurality of times.

Figure 5:
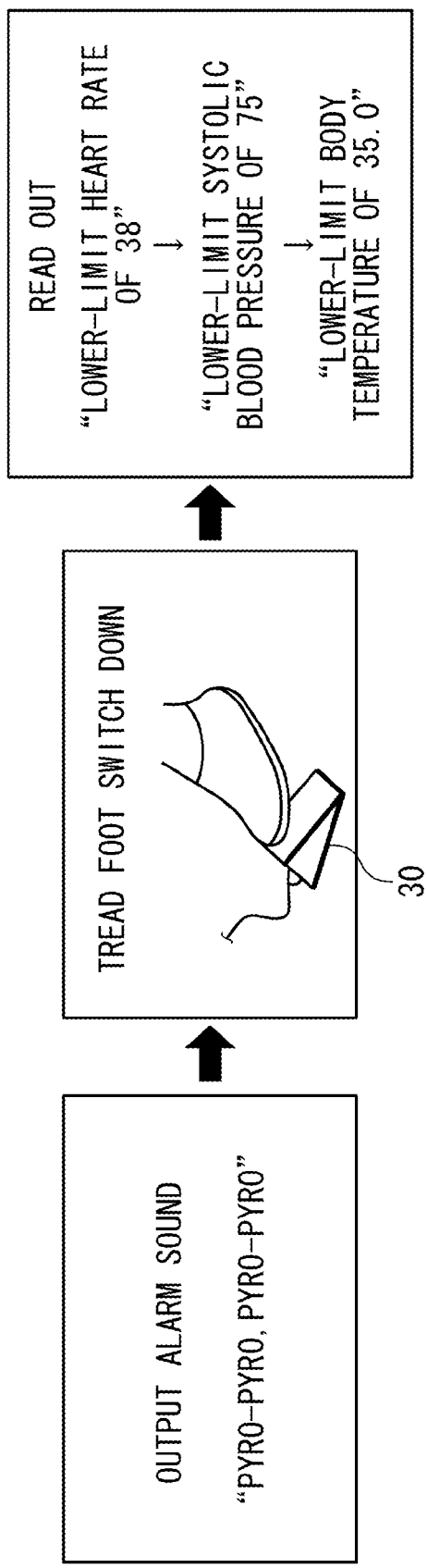
FIG. 5 is a drawing illustrating an example operation flow that differs from the flow shown in FIG. 4.

FIG. 5 illustrates a processing flow employed when abnormal conditions have occurred in a plurality of parameters of the measured physiological signal; for instance, in this case when an abnormal condition has occurred in each of the heart rate (HR), the invasive blood pressure value (ART), and the body temperature (TEMP). The alarm sound "pyro-pyro, pyro-pyro" that notifies occurrence of an abnormal condition is output from the notification unit 23. In relation to the alarm sound, there is output an alarm sound assigned to an abnormality that requires medical treatment of highest urgency among a plurality of occurred abnormalities. Moreover, as described by reference to FIG. 4, the melody of the alarm sound shows highest urgency for medical treatment. Consequently, the alarm sound shown in FIG. 5 shows an alarm sound that exhibits high urgency from the viewpoint of the three phases of the settings shown in FIG. 4.

Subsequently, when the healthcare personnel treads the foot switch 30 down with foot, the alarm inactivate signal is output from the foot switch 30. In accordance with the alarm inactivate signal, the alarm control section 15 stops the alarm sound "pyro-pyro, pyro-pyro" being output from the notification unit 23, thereby inactivating the alarm. After inactivating the alarm, the alarm control section 15 outputs by voice in sequence contents of all of the plurality of sets of physiological parameter by which the alarm is determined to be generated. To be specific, a "lower-limit heart rate of 38," a "lower-limit systolic arterial blood pressure of 75," and a "lower-limit body temperature of 35.0." It is notified that an abnormal condition in the value of the measured heart rate has been detected and that the thus-detected value is 38 [bpm] which falls below the lower-limit threshold value. Next, it is also notified that an abnormal condition in the blood pressure value has been detected and that the systolic arterial blood pressure is 75 [mmHg] which falls below the lower-limit threshold value. Moreover, it is notified that an abnormal condition in the body temperature has been detected and that the value of the body temperature is 35.0 [degrees centigrade] which falls below the threshold value.

When abnormal conditions exist in the plurality of sets of physiological parameter, the physiological parameter are read out in a descending order from a set of physiological parameter that exhibit high urgency for medical treatment. Therefore, in the case shown in FIG. 5, it can be ascertained that medical treatment for the abnormal condition in heart rate shows high urgency; that a medical treatment for the abnormal condition in blood pressure value shows the second high urgency; and that a medical treatment for the abnormal condition in body temperature shows low urgency.

A circumstance in which use of the foot switch 30 is desirable on occurence of an alarm includes; for instance, a circumstance in which the healthcare personnel needs to carefully observe the patient as in a case where the patient is in the course of undergoing medical treatment or surgery and where the healthcare personnel is fully occupied with the treatment or surgery. When an alarm is generated as a result of the condition of the patient having turned for the worse, the healthcare personnel must look aside from the patient to ascertain contents of the alarm displayed on the display section 22 when using a traditional monitor. In addition, if the healthcare personnel attempts to push the alarm inactivate button 21, he/she must suspend the treatment, or the like, touching the alarm inactivate button 21 on the display screen by hand when using a traditional monitor. Meanwhile, the healthcare personnel can ascertain the contents of the alarm; namely, contents of the physiological parameter that are abnormal, by means of depressing (treading down) only the foot switch 30 without suspending the treatment, or the like, with the constant eye on the patient when using the physiological monitoring apparatus according to the present subject matter.

In addition, the circumstance in which the use of the foot switch 30 is desirable at the time of issuance of the alarm includes; for instance, a circumstance in which the healthcare personnel is in the middle of performing medical treatment for an affected infant in the NICU. In the NICU, the affected infant is in an infant incubator in many cases, and the healthcare personnel performs medical treatment or care for the infant with both hands in the incubator. Further, in the NICU, the physiological monitoring apparatus is often installed at an elevated position above the incubator. With the traditional monitor, when ascertaining the display section 22 of the monitor as a result of occurence of the alarm, the healthcare personnel must visually check the display section 22 while looking aside from the infant. Furthermore, if the healthcare personnel attempts to push the alarm inactivate button 21, he/she must pull the hand out of the incubator to touch the alarm inactivate button 21 by hand. With the physiological monitoring apparatus of the present subject matter, even in such a circumstance, the healthcare personnel can ascertain the contents of the alarm; namely, details of physiological parameter indicating the abnormal condition, by means of depressing (treading down) only the foot switch 30 without suspending the treatment, or the like, with the constant eye on the patient.

The configuration described above in connection with the embodiment enables inactivation of the alarm by means of depressing (treading down) only the foot switch 30 when an alarm is generated as a result of occurrence of an abnormal condition in the physiological parameter. Further, in addition to inactivation of the alarm, contents of abnormal physiological parameter for which the alarm is being generated (e.g., parameters of physiological signal, a measured value, and the like) can be notified by voice. Even in the middle of performing surgery that cannot be quit halfway (e.g., medical treatment or surgical operation of a patient), the healthcare personnel can ascertain details of the abnormal physiological parameter without suspending surgery and with the attention focused on surgery, so that accurate treatment and judgment can be performed.

Moreover, when an abnormal condition in physiological parameter has occurred in connection with a plurality of parameters in an overlapping manner and when there are a plurality of sets of physiological parameter by which the alarm is determined to be generated, contents of all sets of physiological parameter for which the alarm is being generated are sequentially output by voice. Accordingly, the number and types of sets of physiological parameter that indicate abnormal condition can be recognized without fail. Therefore, the healthcare personnel can tread the foot switch 30 down and practice appropriate medical treatment.

Further, when contents of the plurality of sets of physiological parameter are output by voice, the physiological parameter are output by voice in a descending order from physiological parameter that exhibit high urgency for medical treatment. Therefore, parameters that require medical treatment in preference can be reliably recognized without fail.

Although the presently disclosed subject matter has been described as above in detail by reference to the specific embodiment, it is manifest to those who are versed in the art that the presently disclosed subject matter be susceptible to various alterations or corrections without departing from the spirit and scope of the subject matter.

The physiological monitoring apparatus of the present subject matter enables the healthcare personnel to inactivate the alarm by treading the foot switch down. Hence, even in the middle of performing surgery that cannot be interrupted halfway, the healthcare personnel can inactivate the alarm without suspending the surgery. In addition, since contents of physiological parameter by which an alarm is determined to be generated are notified by voice, the healthcare personnel can ascertain the contents of the alarm without fail.

What is claimed is:

1. A physiological monitoring apparatus comprising:
notification unit configured to notify an alarm;
an alarm determination section configured to determine whether or not to generate the alarm by comparing measured physiological parameter pertinent to a patient with a predetermined threshold value;
an alarm control section configured to let the notification unit generate the alarm when the alarm determination section has determined to generate the alarm; and
a foot switch configured to, when being trodden, output to the alarm control section an alarm inactivate signal for inactivating the alarm, wherein
the alarm control section inactivates the alarm being notified by the notification unit in accordance with the alarm inactivate signal output from the foot switch, and lets the notification unit notify by voice a content of physiological parameter from which generating the alarm has been determined.

2. The physiological monitoring apparatus according to claim 1, wherein, when the foot switch is trodden in a case where a plurality of sets of physiological parameter by which the alarm is being generated are existing, the alarm control section lets the notification unit notify by voice contents of a plurality of sets of physiological parameter from which generating the alarm has been determined.

3. The physiological monitoring apparatus according to claim 2, wherein, when letting the notification unit sequentially notify contents of the plurality of sets of physiological parameter, the alarm control section lets the notification unit notify the physiological parameter in a descending order from physiological parameter that indicates high urgency for medical treatment.

* * * * *